(12) United States Patent
Diamandis

(10) Patent No.: US 6,962,793 B2
(45) Date of Patent: Nov. 8, 2005

(54) METHODS FOR DETECTING ALZHEIMERS DISEASE

(75) Inventor: Eleftherios P. Diamandis, Toronto (CA)

(73) Assignee: Mount Sinai Hospital, Ontario (CA)

( * ) Notice: Subject to any disclaimer, the term of this patent is extended or adjusted under 35 U.S.C. 154(b) by 86 days.

(21) Appl. No.: 10/036,308

(22) Filed: Oct. 26, 2001

(65) Prior Publication Data

US 2002/0182644 A1 Dec. 5, 2002

Related U.S. Application Data

(60) Provisional application No. 60/243,670, filed on Oct. 27, 2000.

(51) Int. Cl.$^7$ .................. G01N 33/53; G01N 33/537; G01N 33/567; C12N 11/00; C01K 16/00
(52) U.S. Cl. .................. 435/7.92; 435/7.1; 435/7.2; 435/7.21; 435/7.4; 435/7.72; 435/7.94; 435/183; 435/174; 436/501; 436/503; 436/548; 530/388.2
(58) Field of Search .................. 435/7.92, 7.1, 435/7.2, 7.21, 7.4, 7.72, 7.94, 183, 174; 436/501, 503, 548; 530/388.2, 350, 395

(56) References Cited

U.S. PATENT DOCUMENTS 5,733,768 A    3/1998   Dixon et al.

FOREIGN PATENT DOCUMENTS

| EP | 1092767 A1 | 4/2001 |
|---|---|---|
| EP | 0576152 B1 | 6/2002 |
| JP | 9-149790 | 6/1997 |
| WO | WO 98/11238 | 3/1998 |

OTHER PUBLICATIONS

Ogawa et al., Psychiatry and Clinical Neurosci., 2000, 54, 419–426.*

Little et al., J. Biol. Chem., 1997, 272, 40, pp. 25135–25251.*

Diamandis, E. et al., "Human Kallikrein 6 (Zyme/Protease M/Neurosin): A New Serum Biomarker of Ovarian Carcinoma", *Clinical Biochemistry*, 33(7):579–583 (2000).

Hoffman, BR et al., "Immunofluorometric quantitation and histochemical localization of kallikrein 6 protein in ovarian cancer tissue: a new independent unfavorable prognostic biomarker", *British Journal of Cancer*, 87:763–771 (2002).

Little, S. et al., "Zyme, a Novel and Potentially Amyloidogenic Enzyme cDNA Isolated from Alzheimer's Disease Brain", *The Journal of Biological Chemistry*, 272(40) 25135–25142 (1997).

Mitsui, S. et al., "Decreased Cerebrospinal Fluid Levels of Neurosin (KLK6), an Aging–Related Protease, as a Possible New Risk Factor for Alzheimer's Disease", *Ann. N.Y. Acad. Sci.*, 977:216–223 (2002).

Ogawa, K. et al., "Localization of a novel type trypsin–like serine protease, neurosin, in brain tissues of Alzheimer's disease and Parkinson's disease", *Psychiatry and Clinical Neurosciences*, 54:419–426 (2000).

Petraki, C. et al., "The Spectrum of Human Kallikrein 6 (Zyme/Protease M/Neurosin) Expression in Human Tissues as Assessed by Immunohistochemistry", *The Journal of Histochemistry & Cytochemistry*, 49(11):1431–1441 (2001).

Yamanaka, H. et al., "Protease M/neurosin mRNA is expressed in mature oligodendrocytes", *Molecular Brain Research*, 71:217–224 (1999).

Yamashiro, K. et al., "Molecular cloning of a novel trypsin–like serine protease (neurosin) preferentially expressed in brain", *Biochimica et Biophysica Acta*, 1350:11–14 (1997).

Yousef, G. et al., "Molecular Characterization of Zyme/Protease M/Neurosin (PRSS9), a Hormonally Regulated Kallikrein–like Serine Protease", *Genomics*, 62(2):251–259 (1999).

Zarghooni, M. et al., "Decreased concentration of human kallikrein 6 in brain extracts of Alzheimer's disease patients", *Clinical Biochemistry*, 35:225–231 (2002).

* cited by examiner

Primary Examiner—Olga N. Chernyshev
(74) Attorney, Agent, or Firm—Merchant & Gould P.C.

(57) ABSTRACT

Methods for diagnosing and monitoring Alzheimer's Disease in a subject comprising measuring hK6 in a sample from the subject. hK6 may be measured using a reagent that detects or binds to hK6, preferably antibodies reactive with hK6.

8 Claims, 5 Drawing Sheets

METHODS FOR DETECTING ALZHEIMERS DISEASE

FIELD OF THE INVENTION

The invention relates to methods for detecting Alzheimer's Disease.

BACKGROUND OF THE INVENTION

Alzheimer's disease (AD) is the major cause of dementia in the elderly. Although rare genetic forms of AD exist, most patients are classified as having sporadic AD, since no family history is usually identified. Pathologically, AD is characterized by neuronal and synaptic degeneration with an increased number of senile plaques and neurofibrillary tangles compared to non-demented individuals of comparable age (1–3).

The senile plaques, characteristic of Alzheimer's disease, are composed of a central core of aggregated beta-amyloid, a breakdown product of amyloid precursor protein (APP) (2). The neurofibrillary tangles are insoluble intracellular thread-like structures made up of a hyberphospholated form of a protein called tau, which is associated with microtubules (4).

Early and accurate diagnosis of Alzheimer's disease is very important since early intervention may delay or arrest the reversible neuronal damage. Clinical diagnosis is not always accurate since the criteria are relatively subjective and the disease needs to be differentiated from other dementing illnesses (5–8). There is a need for developing biochemical diagnostic markers that could aid in the diagnosis of early Alzheimer's disease and also for monitoring treatment.

Cerebrospinal fluid (CSF) is one of the preferred clinical samples for biomarker analysis in Alzheimer's disease since it is in direct contact with the extracellular space of the brain. The discovery of serum or urine biomarkers for this disease is more preferable, due to the ease of collecting blood or urine, in comparison to CSF. Currently, two biochemical markers are used as aids for diagnosing Alzheimer's disease, including CSF-total tau and CSF-amyloid beta-42 (Aβ-42) (9–25). The latter is a major component of the senile plaques while the former is a component of intracellular neurofibrillary tangles. In Alzheimer's disease, CSF-total tau is increased and CSF-Aβ-42 is decreased. These two markers, either alone or in combination, are quite useful but by no means 100% sensitive or specific for Alzheimer's disease. Moreover, serum analysis of these biomarkers for diagnosis and monitoring is not particularly useful. More recently, another biomarker, neuronal thread protein and its derivatives, appears to be increased in cerebrospinal fluid and urine of patients with Alzheimer's disease but its sensitivity and specificity are not perfect either (26–29). For these reasons, there is a need for developing new biomarkers for serum and CSF analysis, for diagnosis and monitoring of Alzheimer's disease.

Human kallikrein 6 (hK6, encoded by the KLK6 gene) is a new member of the kallikrein gene family, which is also known as zyme/protease M/neurosin (30–33). This is a secreted serine protease which has recently been found in many biological fluids and tissues (34). Little et al. have reported that this protein may have amyloidogenic potential in the brain and may contribute to the pathogenesis of Alzheimer's disease (30). Until recently, no methods were available for the quantitative measurement of hK6 in biological fluids and tissues.

SUMMARY OF THE INVENTION

A highly sensitive hK6 immunoassay for the measurement of hK6 in various biological fluids was developed (Example 1). Using this sensitive assay the concentration of hK6 in brain tissue extracts obtained from Alzheimer's disease brains or control subjects as well as the analysis of serum and CSF from Alzheimer's disease patients or control subjects were analyzed. The present inventors found significant differences in hK6 concentration in both the tissues and the two biological fluids. hK6 analysis in cerebrospinal fluid and serum may aid in the diagnosis of Alzheimer's disease.

The present invention relates to a method for detecting Alzheimer's disease in a subject comprising detecting hK6 in a sample from the subject. hK6 may be measured using a reagent that detects or binds to hK6 preferably antibodies specifically reactive with hK6 or a part thereof.

In an aspect of the invention, a method is provided for detecting hK6 associated with Alzheimer's disease in a subject or patient comprising:

(a) taking a sample derived from a subject or patient;

(b) detecting or identifying in the sample hK6; and (c) comparing the detected amount with an amount detected for a standard.

The invention also relates to a method of screening a subject for Alzheimer's disease comprising:

(a) obtaining a serum or cerebrospinal fluid sample from a subject;

(b) detecting the amount of hK6 in said sample; and (c) comparing said amount of hK6 detected to a predetermined standard, where detection of a level of hK6 greater than that of a standard is indicative of Alzheimer's Disease.

The invention also relates to a method for diagnosing and monitoring Alzheimer's Disease in a subject by detecting hK6 in a sample from the subject comprising:

(a) contacting a biological sample from the subject with an antibody specific for hK6 which is directly or indirectly labelled with a detectable substance;

(b) detecting the detectable substance to detect hK6 in the sample;

(c) comparing the detected level of hK6 to levels obtained for samples from healthy control subjects or from other samples of the subject.

The terms "detecting" or "detect" include assaying, quantitating, imaging or otherwise establishing the presence or absence of the target hK6, subunits thereof, or combinations of reagent bound targets, and the like, or assaying for, imaging, ascertaining, establishing, or otherwise determining one or more factual characteristics of Alzheimer's Disease. The term encompasses diagnostic, prognostic, and monitoring applications for hK6.

In an embodiment, the invention relates to a method for diagnosing and monitoring Alzheimer's Disease in a subject by quantitating hK6 in a biological sample from the subject comprising (a) reacting the biological sample with an antibody specific for hK6 which is directly or indirectly labelled with a detectable substance; and (b) detecting the detectable substance.

Embodiments of the methods of the invention involve (a) reacting a biological sample from a subject with an antibody specific for hK6 which is directly or indirectly labelled with an enzyme; (b) adding a substrate for the enzyme wherein the substrate is selected so that the substrate, or a reaction product of the enzyme and substrate, forms fluorescent complexes; (c) quantitating hK6 in the sample by measuring fluorescence of the fluorescent complexes; and (d) comparing the quantitated levels to levels obtained for other samples from the subject patient, or control subjects. In an embodiment the quantitated levels are compared to levels quantitated for subjects without Alzheimer's Disease wherein an increase in hK6 levels compared with the control subjects is indicative of Alzheimer's Disease.

A preferred embodiment of the invention comprises the following steps
- (a) incubating a biological sample with a first antibody specific for hK6 which is directly or indirectly labeled with a detectable substance, and a second antibody specific for hK6 which is immobilized;
- (b) separating the first antibody from the second antibody to provide a first antibody phase and a second antibody phase;
- (c) detecting the detectable substance in the first or second antibody phase thereby quantitating hK6 in the biological sample; and
- (d) comparing the quantitated hK6 with a standard.

A standard may correspond to levels quantitated for samples from healthy control subjects, or from other samples of the subject. Increased levels of hK6 as compared to the standard may be indicative of Alzheimer's Disease.

According to an aspect of the invention, a method for imaging Alzheimer's Disease is provided comprising:
- (a) injecting a patient with an agent that binds to kallikrein 6, the agent carrying a label for imaging;
- (b) allowing the agent to incubate in vivo and bind to kallikrein 6 associated with the chorioid plexus of the brain;
- (c) detecting the presence of the label localized to the chorioid plexus of the brain.

In an embodiment of the invention the agent is an antibody which recognizes kallikrein 6. In another embodiment of the invention the agent is a chemical entity which recognizes kallikrein 6.

The agent carries a label to image kallikrein 6. Examples of labels useful for imaging are radiolabels, fluorescent labels (e.g fluorescein and rhodamine), nuclear magnetic resonance active labels, positron emitting isotopes detectable by a positron emission tomography ("PET") scanner, chemiluminescers such as luciferin, and enzymatic markers such as peroxidase or phosphatase. Short-range radiation emitters, such as isotopes detectable by short-range detector probes can also be employed The invention also relates to kits for carrying out the methods of the invention.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF THE DRAWINGS

The invention will now be described in relation to the drawings in which.

DETAILED DESCRIPTION OF THE INVENTION

Figure 1:
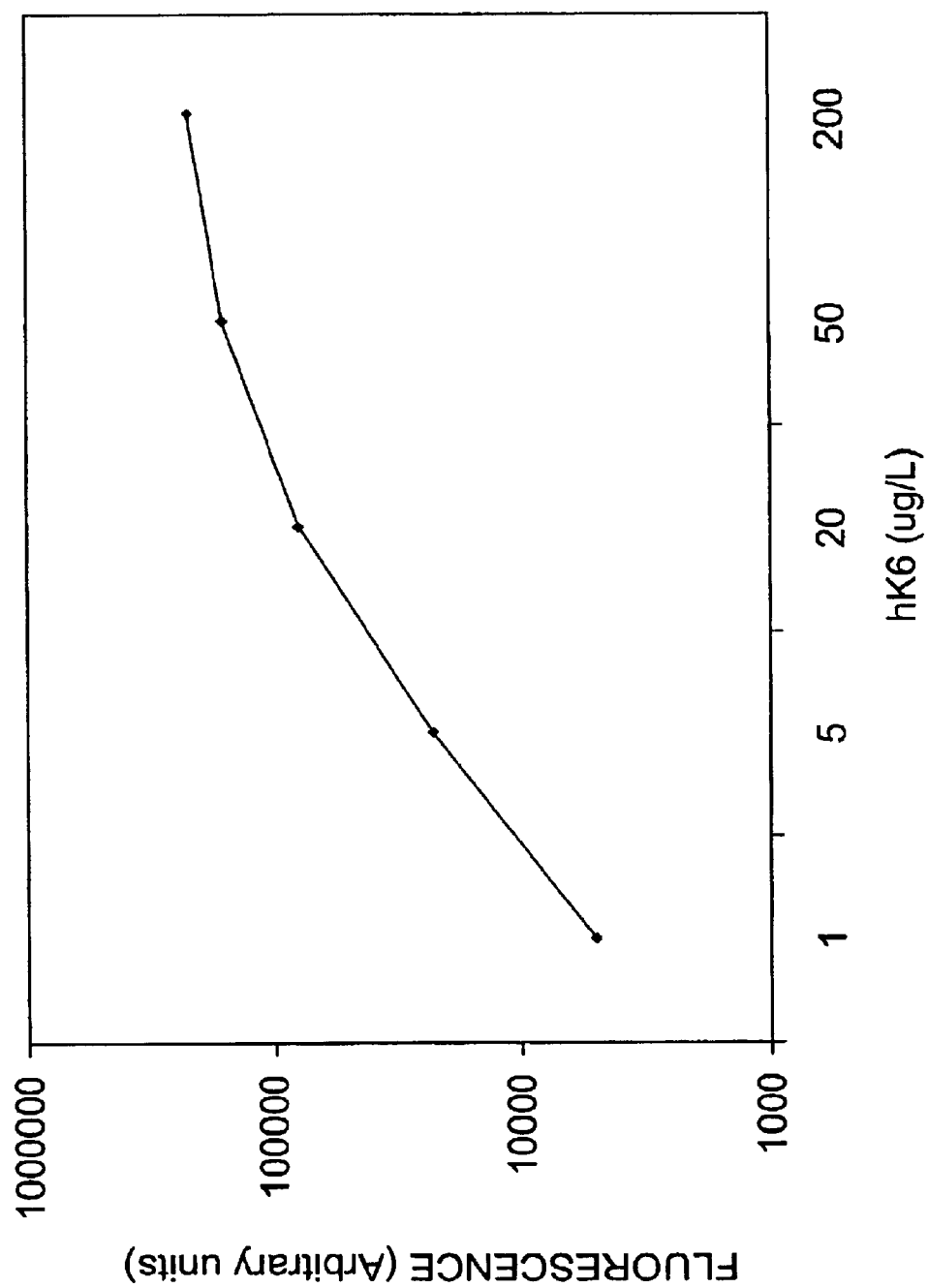
FIG. 1: Calibration curve of the newly developed hK6 protein assay. The fluorescence of the zero standard (~18,000 arbitrary fluorescence units) was subtracted from all other measurements.

As hereinbefore mentioned, the present invention provides a method for detecting Alzheimer's Disease in a subject by detecting hK6 in a biological sample from the subject comprising reacting the sample with a reagent that binds to hK6, preferably an antibody specific for hK6 which is directly or indirectly labelled with a detectable substance, and detecting the detectable substance.

The terms "sample", "biological sample", and the like mean a material known to or suspected of containing or expressing hK6. The test sample can be used directly as obtained from the source or following a pretreatment to modify the character of the sample. The sample can be derived from any biological source, such as tissues or extracts, including cells, and physiological fluids, such as, for example, whole blood, plasma, serum, saliva, ocular lens fluid, cerebrospinal fluid, sweat, urine, milk, ascites fluid, synovial fluid, peritoneal fluid and the like. The sample can be obtained from animals, preferably mammals, most preferably humans. The sample can be treated prior to use, such as preparing plasma from blood, diluting viscous fluids, and the like. Methods of treatment can involve filtration, distillation, extraction, concentration, inactivation of interfering components, the addition of reagents, and the like. In a preferred embodiment, the biological sample is a biological fluid, more preferably cerebrospinal fluid or blood.

In embodiments of the invention, the method described herein is adapted for diagnosing and monitoring Alzheimer's Disease by quantitating hK6 in biological samples from a subject. These applications require that the amount of hK6 quantitated in a sample from a subject being tested be compared to levels quantitated for another sample or an earlier sample from the subject, or levels quantitated for a control sample. Levels for control samples from healthy subjects maybe established by prospective and/or retrospective statistical studies. Healthy subjects who have no clinically evident disease or abnormalities may be selected for statistical studies. Diagnosis maybe made by a finding of statistically different levels of hK6 compared to a control sample or previous levels quantitated for the same subject.

The term "hK6" refers to human kallikrein 6, (also known as zyme, protease M, and neurosin) a trypsin-like serine protease of 244 amino acids in length, of which 16 amino acids constitute the signal peptide and 5 amino acids, the activation peptide (30, 31, and 32). The term includes all homologs, naturally occurring allelic variants, isoforms and precursors of human kallikrein 6 of GenBank Accession Nos. AF013988, AF149289, HSU62801, D78203, and NM002774. In general for example, naturally occurring allelic variants of human kallikrein 6 will share significant homology (70–90%) to the sequences shown in GenBank Accession Nos.

AF013988, AF149289, HSU62801, D78203, and NM002774. Allelic variants may contain conservative amino acid substitutions from the KLK6 sequence or will contain a substitution of an amino acid from a corresponding position in a hK6 homologue such as, for example, the murine kallikrien 6 homologue.

The term "subject" refers to a warm-blooded animal such as a mammal which is afflicted with, or suspected to be afflicted with Alzheimer's Disease. Preferably, "subject" refers to a human.

The antibodies specific for hK6 used in the methods of the invention may be obtained from scientific or commercial sources. Alternatively, isolated native hK6 or recombinant hK6 may be utilized to prepare antibodies, monoclonal or polyclonal antibodies, and immunologically active fragments (e.g. a Fab or (Fab)$_2$ fragment), an antibody heavy chain, an antibody light chain, humanized antibodies, a genetically engineered single chain F$_v$ molecule (Ladner et al, U.S. Pat. No. 4,946,778), or a chimeric antibody, for example, an antibody which contains the binding specificity of a murine antibody, but in which the remaining portions are of human origin. Antibodies including monoclonal and polyclonal antibodies, fragments and chimeras, may be prepared using methods known to those skilled in the art. Preferably, antibodies used in the methods of the invention are reactive against hK6 if they bind with a K$_a$ of greater than or equal to $10^{-7}$ M. In a sandwich immunoassay of the invention mouse polyclonal antibodies and rabbit polyclonal antibodies are utilized.

Antibodies specifically reactive with hK6, or derivatives, such as enzyme conjugates or labeled derivatives, may be used to detect hK6 in various biological samples, for example they may be used in any known immunoassays which rely on the binding interaction between an antigenic determinant of a protein and the antibodies. Examples of such assays are radioimmunoassays, enzyme immunoassays (e.g. ELISA), immunofluorescence, immunoprecipitation, latex agglutination, hemagglutination, and histochemical tests.

An antibody specific for hK6 may be labelled with a detectable substance and localised or identified in biological samples based upon the presence of the detectable substance. Examples of detectable substances include, but are not limited to, the following: radioisotopes (e.g.,$^3$H, $^{14}$C, $^{35}$S, $^{125}$I, $^{131}$I), fluorescent labels (e.g., FITC, rhodamine, lanthanide phosphors), luminescent labels such as luminol; enzymatic labels (e.g., horseradish peroxidase, beta-galactosidase, luciferase, alkaline phosphatase, acetylcholinesterase), biotinyl groups (which can be detected by marked avidin e.g., streptavidin containing a fluorescent marker or enzymatic activity that can be detected by optical or calorimetric methods), predetermined polypeptide epitopes recognized by a secondary reporter (e.g., leucine zipper pair sequences, binding sites for secondary antibodies, metal binding domains, epitope tags). Indirect methods may also be employed in which the primary antigen-antibody reaction is amplified by the introduction of a second antibody, having specificity for the antibody reactive against hK6. By way of example, if the antibody having specificity against hK6 is a rabbit IgG antibody, the second antibody may be goat anti-rabbit gamma-globulin labelled with a detectable substance as described herein.

Methods for conjugating or labelling the antibodies discussed above may be readily accomplished by one of ordinary skill in the art. (See for example Inman, Methods In Enzymology, Vol. 34, Affinity Techniques, Enzyme Purification: Part B, Jakoby and Wichek (eds.), Academic Press, New York, p. 30, 1974; and Wilchek and Bayer, "The Avidin-Biotin Complex in Bioanalytical Applications," Anal. Biochem. 171:1–32, 1988 re methods for conjugating or labelling the antibodies with enzyme or ligand binding partner).

Time-resolved fluorometry may be used to detect a signal. For example, the method described in Christopoulos TK and Diamandis EP Anal Chem 1992:64:342–346 may be used with a conventional time-resolved fluorometer.

Therefore, in accordance with an embodiment of the invention, a method is provided wherein a hK6 antibody is labelled with an enzyme, a substrate for the enzyme is added wherein the substrate is selected so that the substrate, or a reaction product of the enzyme and substrate, forms fluorescent complexes with a lanthanide metal. A lanthanide metal is added and hK6 is quantitated in the sample by measuring fluorescence of the fluorescent complexes. The antibodies specific for hK6 may be directly or indirectly labelled with an enzyme. Enzymes are selected based on the ability of a substrate of the enzyme, or a reaction product of the enzyme and substrate, to complex with lanthanide metals such as europium and terbium. Examples of suitable enzymes include alkaline phosphatase and β-galactosidase. Preferably, the enzyme is alkaline phosphatase. The hK6 antibodies may also be indirectly labelled with an enzyme. For example, the antibodies may be conjugated to one partner of a ligand binding pair, and the enzyme may be coupled to the other partner of the ligand binding pair. Representative examples include avidin-biotin, and riboflavin-riboflavin binding protein. Preferably the antibodies are biotinylated, and the enzyme is coupled to streptavidin.

In the method, antibody bound to hK6 in a sample is detected by adding a substrate for the enzyme. The substrate is selected so that in the presence of a lanthanide metal (e.g. europium, terbium, samarium, and dysprosium, preferably europium and terbium), the substrate, or a reaction product of the enzyme and substrate, forms a fluorescent complex with the lanthanide metal. Examples of enzymes and substrates for enzymes that provide such fluorescent complexes are described in U.S. Pat. No. 5,3112,922 to Diamandis. By way of example, when the antibody is directly or indirectly labelled with alkaline phosphatase the substrate employed in the method may be 4-methylumbelliferyl phosphate, or 5-fluorosalicyl phosphate. The fluorescence intensity of the complexes is typically measured using a time-resolved fluorometer e.g. a CyberFluor 615 Imunoanalyzer (Nordion International, Kanata, Ontario).

The sample, antibody specific for hK6, or hK6, may be immobilized. Examples of suitable carriers are agarose, cellulose, dextran, Sephadex, Sepharose, liposomes, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, well, beads, disc, sphere etc. The immobilized antibody may be prepared by reacting the material with a suitable insoluble carrier using known chemical or physical methods, for example, cyanogen bromide coupling.

In accordance with an embodiment, the present invention provides means for determining hK6 in a blood sample by measuring hK6 by immunoassay. A variety of immunoassay methods can be used to measure hK6. In general, an hK6 immunoassay method may be competitive or noncompetitive. Competitive methods typically employ an immobilized or immobilizable antibody to hK6 (anti-hK6) and a labeled form of hK6. Sample hK6 and labeled hK6 compete for binding to anti-hK6. After separation of the resulting labeled hK6 that has become bound to anti-hK6 (bound fraction) from that which has remained unbound (unbound fraction), the amount of the label in either bound or unbound fraction is measured and may be correlated with the amount of hK6 in the test sample in any conventional manner, e.g., by comparison to a standard curve.

Preferably a non-competitive method is used for the determination of hK6, with the most common method being the "sandwich" method. In this assay, two anti-hK6 antibodies are employed. One of the anti-hK6 antibodies is directly or indirectly labeled (sometimes referred to as the "detection antibody") and the other is immobilized or immobilizable (sometimes referred to as the "capture antibody"). The capture and detection antibodies can be contacted simultaneously or sequentially with the test sample. Sequential methods can be accomplished by incubating the capture antibody with the sample, and adding the detection antibody at a predetermined time thereafter (sometimes referred to as the "forward" method); or the detection antibody can be incubated with the sample first and then the capture antibody added (sometimes referred to as the "reverse" method). After the necessary incubation(s) have occurred, to complete the assay, the capture antibody is separated from the liquid test mixture, and the label is measured in at least a portion of the separated capture antibody phase or the remainder of the liquid test mixture. Generally it is measured in the capture antibody phase since it comprises hK6 bound by ("sandwiched" between) the capture and detection antibodies.

In a typical two-site immunometric assay for hK6, one or both of the capture and detection antibodies are polyclonal antibodies. The label used in the detection antibody can be selected from any of those known conventionally in the art. The label may be an enzyme or a chemiluminescent moiety, but it can also be a radioactive isotope, a fluorophor, a detectable ligand (e.g., detectable by a secondary binding by a labeled binding partner for the ligand), and the like. Preferably the antibody is labelled with an enzyme which is detected by adding a substrate that is selected so that a reaction product of the enzyme and substrate forms fluorescent complexes. The capture antibody is selected so that it provides a means for being separated from the remainder of the test mixture. Accordingly, the capture antibody can be introduced to the assay in an already immobilized or insoluble form, or can be in a immobilizable form, that is, a form which enables immobilization to be accomplished subsequent to introduction of the capture antibody to the assay. An immobilized capture antibody may comprise an antibody covalently or noncovalently attached to a solid phase such as a magnetic particle, a latex particle, a microtiter plate well, a bead, a cuvette, or other reaction vessel. An example of an immobilizable capture antibody is antibody which has been chemically modified with a ligand moiety, e.g., a hapten, biotin, or the like, and which can be subsequently immobilized by contact with an immobilized form of a binding partner for the ligand, e.g., an antibody, avidin, or the like. In an embodiment, the capture antibody may be immobilized using a species specific antibody for the capture antibody that is bound to the solid phase.

A particular sandwich immunoassay method of the invention employs two antibodies reactive against hK6, a second antibody having specificity against an antibody reactive against hK6 labelled with an enzymatic label, and a fluorogenic substrate for the enzyme. In an embodiment, the enzyme is alkaline phosphatase (ALP) and the substrate is 5-fluorosalicyl phosphate. ALP cleaves phosphate out of the fluorogenic substrate, 5-fluorosalicyl phosphate, to produce 5-fluorosalicylic acid (FSA). 5-Fluorosalicylic acid can then form a highly fluorescent ternary complex of the form FSA-Tb(3+)-EDTA, which can be quantified by measuring the Tb3+ fluorescence in a time-resolved mode. Fluorescence intensity is typically measured using a time-resolved fluorometer e.g. a CyberFluor 615 Imunoanalyzer (Nordion International, Kanata, Ontario).

The above-described immunoassay methods and formats are intended to be exemplary and are not limiting since, in general, it will be understood that any immunoassay method or format can be used in the present invention.

The methods of the invention can be carried out using a diagnostic kit for quantitating hK6 in a sample. By way of example, the kit may contain antibodies specific for hK6, antibodies against the antibodies labelled with an enzyme; and a substrate for the enzyme. The kit may also contain microtiter plate wells, standards, assay diluent, wash buffer, adhesive plate covers, and/or instructions for carrying out a method of the invention using the kit.

The following non-limiting examples are illustrative of the present invention:

EXAMPLE 1

Immunofluorometric Assay of Human Kallikrein 6 (Zyme/Protease M/Neurosin)

Materials and Methods

Diflunisal phosphate (DFP) was synthesized in the laboratory (diflunisal, obtained from Sigma Chemical Co., St. Louis, Mo.). The stock solution of DFP was 0.01 mol/L in 0.1 mol/L NaOH. DFP stock solutions are stable at 4° C. for at least 6 months. Alkaline phosphatase-labeled goat anti-rabbit IgG (GARIg-ALP) and sheep anti-mouse immunoglobulin G (Fc fragment-specific) were obtained from Jackson Immunoresearch, West Grove, Pa. Working solutions of GARIg-ALP were prepared by diluting the stock solution 3,000-fold in the assay buffer (described below). White, opaque 12-well polystyrene microtiter strips were obtained from Dynatech Labs., Alexandria, Va. The substrate buffer was a Tris buffer (0.1 mol/L, pH 9.1) containing 0.1 mol of NaCl and 1 mmol of $MgCl_2$ per liter. The substrate working solution (DFP, 1 mmol/L in substrate buffer) was prepared just before use by diluting the DFP stock solution 10-fold in the substrate buffer. The wash solution was prepared by dissolving 9 g of NaCl and 0.5 g of polyoxyethylenesorbitan monolaurate (Tween 20) in 1 L of a 10 mmol/L Tris buffer, pH 7.40. The developing solution contained 1 mol of Tris base, 0.4 mol of NaOH, 2 mmol of $TbCl_3$ and 3 mmol of EDTA per liter (no pH adjustment). The assay buffer A was a 50 mmol/L Tris buffer, pH 7.40, containing 60 g of BSA, 0.5 g of sodium azide, 100 mL of normal goat serum, 25 mL of normal mouse serum, 5 g of bovine IgG and 0.5 g of Tween 20 per liter. The assay buffer B was the same as assay buffer A except that mouse serum was omitted.

Clinical Samples

Several clinical samples were used to examine the presence of hK6. These included serum and urine samples from male and female individuals (healthy blood donors), breast cyst fluids obtained by needle aspiration, breast tumor cytosolic extracts, prepared as described previously (11), amniotic fluids, milks from lactating women, seminal plasmas, nipple aspirate fluids (NAFs) and cerebrospinal fluids (CSFs). In addition, a panel of human tissue cytosolic extracts, prepared as previously described were tested (Hassapoglidou, S. et al *Oncogene* 1993, 8:1501–1509.). To establish optimal measuring conditions, all samples were tested at various dilutions. The procedures are in accordance with the ethical standards of the Helsinki Declaration of 1975, as revised in 1983.

All tissues and fluid samples were stored at −80° C. until use.

Instrumentation

A time-resolved fluorometer, the CyberFluor 615 Immunoanalyzer (MDS Nordion, Kanata, ON, Canada) was used to measure $Tb^{3+}$ fluorescence in white microtiter wells. This procedure has been described in detail elsewhere (Christopoulos, T K, et al *Anal Chem* 1992, 64:342–346, Ferguson R A et al, *Clin Chem* 1996 42: 675–684).

Procedures

Production and purification of recombinant hK6 protein. Human 293 cells transfected with a plasmid containing the 1.4-kb hK6 cDNA were subjected to selection by growth in G418 (400 mg/L) for three weeks, after which time stable transformants were isolated. One clone generated identifiable amounts of hK6 protein in the culture medium. This cell line was cultured and the tissue culture supernatant was collected and concentrated by using Centricon ultrafiltration devices (Millipore, Waltham, Mass. 02454). Purification of hK6 from the concentrated cell culture supernatants was achieved by reversed-phase high pressure liquid chromatography (C-8, Aquapore RP-300, 0.45×25 cm, Applied Biosystems, Foster City, Calif.) using a linear gradient of 0.1% trifluoroacetic acid/acetonitrile. Generally, the gradient increased at a rate of 1% acetonitrile per min. Factions containing hK6 were located by SDS-polyacrylamide gel electrophoresis, collected, lyophylized and stored at −20° C. (Little SP et al, *J. Bil Chem* 1997:272:25135–25142).

Development of polyclonal antibodies against hK6. Purified recombinant hK6 protein was used to immunize rabbits and mice using standard procedures (*Campbell Am, Production and purification of antibodies. In: Immunoassay. Diamandis E P Christopoulos T K* (eds)00. 95–115, Academic Press, San Diego, 1996). The rabbit and mice antisera were used for the development of the immunofluorometric assay without further purification.

Coating of microtiter plates with sheep anti-mouse immunoglobulin. White polystyrene microtiter wells were coated by incubating overnight 500 ng /100 µL per well of the coating antibody diluted in a 50 mmol/L Tris buffer, pH 7.80. The wells were then washed six times with the wash solution and blocked for 1 hour with 200 µL/well of the blocking solution (10 g/L BSA in 50 mmol/L Tris, pH 7.80). After another six washes, the wells were ready to use.

hK6 calibration. hK6 calibrators of 0, 1, 5, 20, 50 and 200 µg/L were prepared by diluting recombinant purified hK6 protein in a 50 mmol/L Tris buffer, pH 7.80, containing 60 g of BSA and 0.5 g of sodium azide per liter.

hK6 assay. Calibrators or samples (100 µL) were pipetted into the microtiter wells and 50 µL of the polyclonal mouse anti-hK6 antiserum, diluted 5,000-fold in assay buffer B, were added. The wells were then incubated with shaking at room temperature for 2 hours and washed six times. To each well, was added 100 µL of rabbit anti-hK6 antibody, diluted 1,000-fold in assay buffer A, incubated for 30 min as described above, and then washed six times. To each well, was added 100 µL of a goat anti-rabbit immunoglobulin, conjugated to alkaline phosphatase, diluted 3,000-fold in assay buffer A and incubated for 30 min, as described above. The wells were then washed six times; 100 µL of 1 mmol/L DFP working substrate solution was added, and the wells were incubated for 10 min, as described above. 100 µL of developing solution was added to each well, the wells were mixed by mechanical shaking for 1 min and the fluorescence was measured with the time-resolved fluorometer. The calibration and data reduction were performed automatically by the CyberFluor 615 Immunoanalyzer.

High performance liquid chromatography (HPLC): Various biological fluids have been fractionated on a gel filtration column, using the procedures described elsewhere (Yu H, Diamandis E P, *Clin Chem* 1993: 39:2108–2114; Diamandis, E P at al *Cliln Chem* 1997:43:1365–1371)). HPLC fractions were collected and analyzed for hK6 with the developed immunofluorometric assay.

RESULTS

Assay Optimization

Two polyclonal antibodies against recombinant hK6 protein were used, one developed in mice and one developed in rabbits. The chosen assay configuration (indirect coating of the wells with a sheep anti-mouse antibody and detection of the immunocomplex with a goat anti-rabbit immunoglobulin, conjugated to alkaline phosphatase) demonstrated good sensitivity (see below) without the need for any purification or conjugation of the primary antibodies. The amounts of antibodies used, the diluents and incubation times of the various assay steps were optimized. Optimal conditions were selected based on the lowest achievable detection limit and best assay linearity and dynamic range. The final conditions are described above.

Calibration Curve, Detection Limit, Precision

A typical calibration curve of the proposed hK6 assay is shown in FIG. 1. The detection limit, defined as the concentration of hK6 corresponding to the fluorescence of the zero calibrator plus two standard deviations, is $\leq 0.5$ µg/L. Within-run and between-runprecision was assessed at various hK6 concentrations between 2–50 µ/L and with various clinical samples. In all cases, the coefficients of variation (CVs) were between 2 and 9%, consistent with the precision of typical microtiter plate-based immunoassays.

Figure 2:
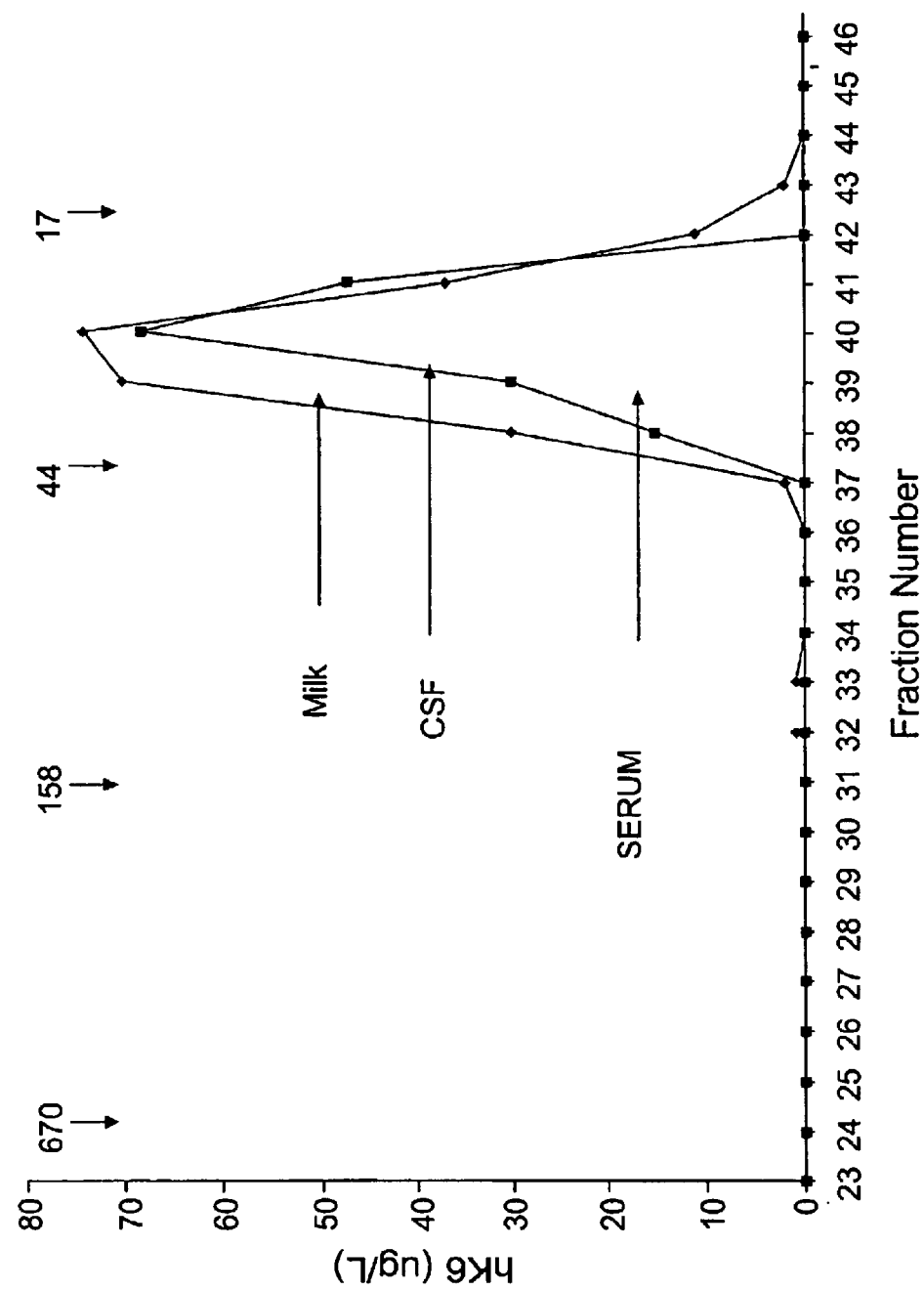
FIG. 2: High performance liquid chromatography separation of three biological fluids and analysis of all fractions with the developed hK6 immunoassay. In all three fluids, a single immunoreactive peak around fractions 38–42 was detected, corresponding to a molecular mass of ~30 kDa. The column was calibrated with molecular weight standards (shown on top with arrows; masses are in kDa). The milk sample was diluted 10 times before injection into the HPLC column.

Specificity hK6 protein was detected in various biological fluids. In order to ensure that the immunofluorometric assay measures hK6 with high sensitivity and specificity, separated in a gel filtration column three biological fluids with relatively high hK6 concentration, (namely one human milk from a lactating woman, one cerebrospinal fluid and one serum sample from an ovarian cancer patient who was found to have high levels of this biomarker in serum) were separated in and measured on a gel filtration column. The results are shown in FIG. 2. In all three biological fluids tested, a single immunoreactive species of a molecular mass of ~30 kDa was detected, which is consistent with the molecular mass of hK6 protein. Higher molecular weight complexes were not detected suggesting that hK6 is present in these biological fluids in its free form. Other serum proteinases (e.g. PSA) are present in serum and other fluids mostly bound to proteinase inhibitors (Stenman U-H, et al, *Cancer Res.* 1991: 51:222–226); Christensson A et al *Cur J Biochem* 1990; 194; 755–763).

hK6 In Biological Fluids and Tissue Extracts

To obtain preliminary information on the presence of hK6 in biological fluids, various clinical samples were analyzed, as shown in Table 1. The highest concentration of hK6 was found in milk of lactating women, followed by cerebrospinal fluid, nipple aspirate fluid and breast cyst fluid. hK6 was also detected in male and female serum samples, in the majority of seminal plasmas and in a relatively small percentage of amniotic fluids and breast tumor cytosolic extracts. hK6 protein was not detected in urine.

Figure 3:
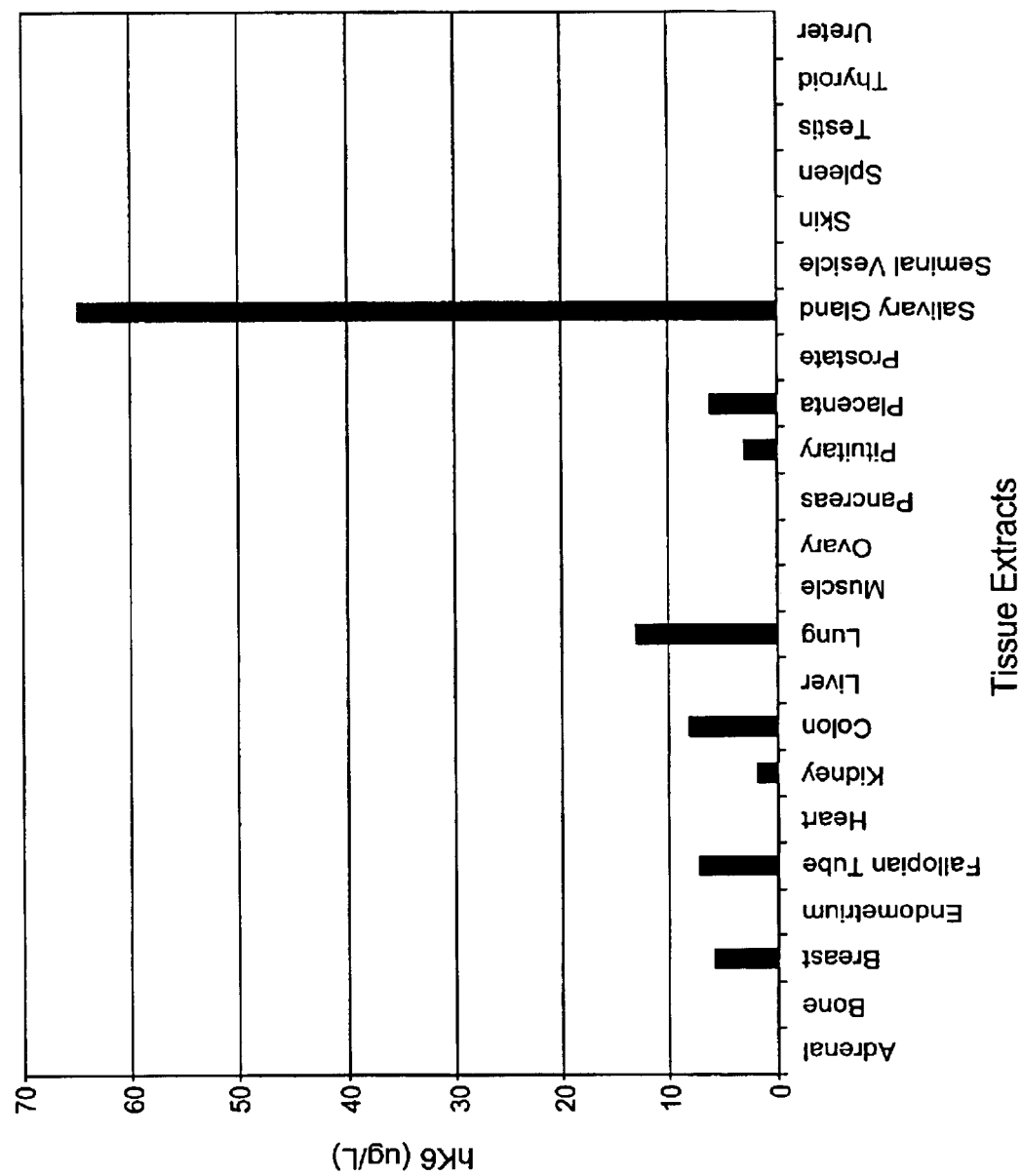
FIG. 3: Analysis of various human tissue cytosolic extracts for hK6 protein.

A number of human tissue cytosolic extracts were also tested. The highest concentration of hK6 was detected in the salivary glands, followed by lung, colon, fallopian tube, placenta, breast, pituitary and kidney. The following tissues tested negative: skin, spleen, bone, thyroid, heart, urerter, liver, muscle, endometrium, testis, pancreas, seminal vesicle, ovary, adrenals and prostate (FIG. 3).

Discussion

The present inventors have developed polyclonal antibodies and an immunofluorometric procedure suitable for quantifying hK6 protein in biological fluids and tissue extracts. Since a rich natural source of hK6 protein is not known, recombinant hK6 protein was used for the development of polyclonal rabbit and mice antibodies. This recombinant protein ensures high purity without any contaminating proteins. The chosen assay configuration does not need any further purification or conjugation of the primary antibodies used, and it is thus a convenient method for developing sensitive immunofluorometric procedures. The same principle has been adopted previously for measuring the p53 tumor suppressor in biological fluids (Hassapoglidou S et al, Oncogene 1993: 8: 1501–1509).

The developed immunoassay for hK6 protein demonstrates good sensitivity, dynamic range and linearity (FIG. 1). It has been further verified that this assay detects a single immunoreactive band in the biological fluids examined. In serum, this proteinase is present in its free form, similarly to observations with hK2 measurements (Black, M H et al Clin Chem 1999; 45:790–799). However, this is in contrast to the situation with PSA, which is known to be present in serum mainly bound to $\alpha_1$-antichymotrypsin (Stenman U-H, et al, Cancer Res. 1991: 51:222–226); Christensson A et al Cur J Biochem 1990; 194; 755–763).

The survey of a relatively large number of biological fluids has indicated that hK6 protein is present at relatively high concentrations in milk of lactating women and other breast secretions, including nipple aspirate fluid and breast cyst fluid (Table 1). Previously, the presence of other kallikreins, including PSA and hK2, has been demonstrated in these biological fluids (Yu, H Diamandis; *Clin Chem* 1995: 41:54–58; Sauter E R et al *Cancer Epidemiol Biomarkers Prevent* 1996 967–970; Diamandis E p et al *Breast Cancer Res Treat* 199638:259–264; Balck M H et al *Br J Cancer* 2000; 82:361–367; Blcak M H et al *Clin Chem* 1999;45: 790–799; yu H. and Diamandis E P *Clin Chem* 1995:41:204–210; Black M H Diamandis E P, *Breast Cancer Res Treat* 200059:1–14). Large amounts of hK6 protein were detected in cerebrospinal fluid, which are consistent with the observation that hK6 is expressed at high levels in brain tissue (Little, supra). hK6 was also found in male and female sera and seminal plasmas and in a small percentage of amniotic fluids and breast tumor cytosols. Previously, PSA and hK2 was demonstrated in these biological fluids as well (Yu, H Diamandis; *Clin Chem* 1995: 41:54–58; Sauter E R et al *Cancer Epidemiol Biomarkers Prevent* 1996 967–970; Diamandis E p et al *Breast Cancer Res Treat* 199638:259–264; Balck M H et al *Br J Cancer* 2000; 82:361–367; Blcak MH et al *Clin Chem* 1999;45: 790–799; yu H. and Diamandis E P *Clin Chem* 1995:41:204–210; Black M H Diamandis E P, *Breast Cancer Res Treat* 200059:1–14). It is interesting to note that although seminal plasma contains extremely high levels of PSA and hK2 (Diamandis E P Trends Endocrinol Metab 1999: 25:14–26' RittenhouseHe et al Crit Rev Clin Lab Sci 1998: 35:275–368), the assay described herein detected very small amounts of hK6 in this biological fluid (Table 1). This further demonstrates that the homologous proteins PSA and hK2 do not have any major cross-reactivity with the developed hK6 assay.

The assay developed here represents the first method for detecting hK6 protein in biological fluids. The results further demonstrate that hK6 is a secreted protein, as predicted by its deduced amino acid sequence (Yousef G M et al Genomics 1999;62:251–259).

EXAMPLE 2

Materials and Methods

Materials and Methods

Immunofluorometric Assay for hK6

The details of this immunofluorometric assay are described in Example 1. The assay utilizes two hK6-specific polyclonal antibodies, one raised in mouse and the other raised in rabbit. This is a non-competitive immunofluorometric procedure which incorporates the principles of time-resolved fluorometry for detection. The assay measures hK6 in the range of 0.5–200 $\mu$/L with precision of less than 10%. All tissue extracts, serum samples and cerebrospinal fluids, were measured at various dilutions to bring the concentrations within the measuring range of the assay.

Clinical Samples

For this preliminary investigation, ten whole blood samples were obtained from patients with histologically-confirmed (post-mortem) Alzheimer's disease, and ten whole blood samples were obtained from normal individuals. Both series of samples were stored at −80° C. until analysis. Since these whole blood samples were hemolyzed, they were centrifuged and the supernatants were diluted 10-fold in a 60 g/L bovine serum albumin solution to minimize the effect of hemolysis.

Ten cerebrospinal fluid samples were also used from patients with confirmed Alzheimer's disease and ten cerebrospinal samples which were collected for investigation of infectious brain pathologies, but tested negative. The CSF samples were analyzed after 100-fold dilution in the diluent described above.

Ten brain tissue specimens were also obtained from the frontal cortex of patients with confirmed Alzheimer's disease and ten frontal cortex brain specimens obtained from patients without Alzheimer's disease. These tissues were pulverized on dry ice to fine powders and they were extracted for preparation of cytosolic extracts essentially as described elsewhere (35). The tissue extracts were centrifuged and the supernatants used for hK6 analysis as well as measurement of total protein. These extracts were analyzed after 100-fold dilution in the diluent described above. The tissues, CSF and blood, were obtained from the same ten individuals; their ages ranged from 61 to 91 with a median of 86 years. There were two males and eight females in this series. The ages of the control subjects (for tissues) ranged from 44 to 81 with a median of 71 years. There were five males and five females in this series.

The tissues and fluids from Alzheimer's disease patients and tissues for the control subjects were obtained from the Institute for Brain Aging and Dementia Tissue Repository, University of California, Irvine, Calif. These specimens were collected within 3.5–6.5 hours post-mortem and were immediately frozen for future use.

RESULTS

The results are summarized in Table 2. The hK6 content of frontal cortex tissue extracts from Alzheimer's disease brains was reduced, in comparison to tissue extracts from control subjects. The average decrease was approximately 2-fold and the differences were of borderline statistical significance (P=0.05–0.07 by t-test or Mann-Whitney test). A statistically highly significant increase of hK6 concentration was observed in cerebrospinal fluid of patients with Alzheimer's disease, in comparison to the control subjects (about 3-fold; P=0.001; Mann-Whitney test). Further, a highly statistically significant increase of hK6 concentration was observed in whole blood of Alzheimer's disease patients, in comparison to control subjects (about 10-fold; P=0.002; Mann-Whitney test).

Figure 4:
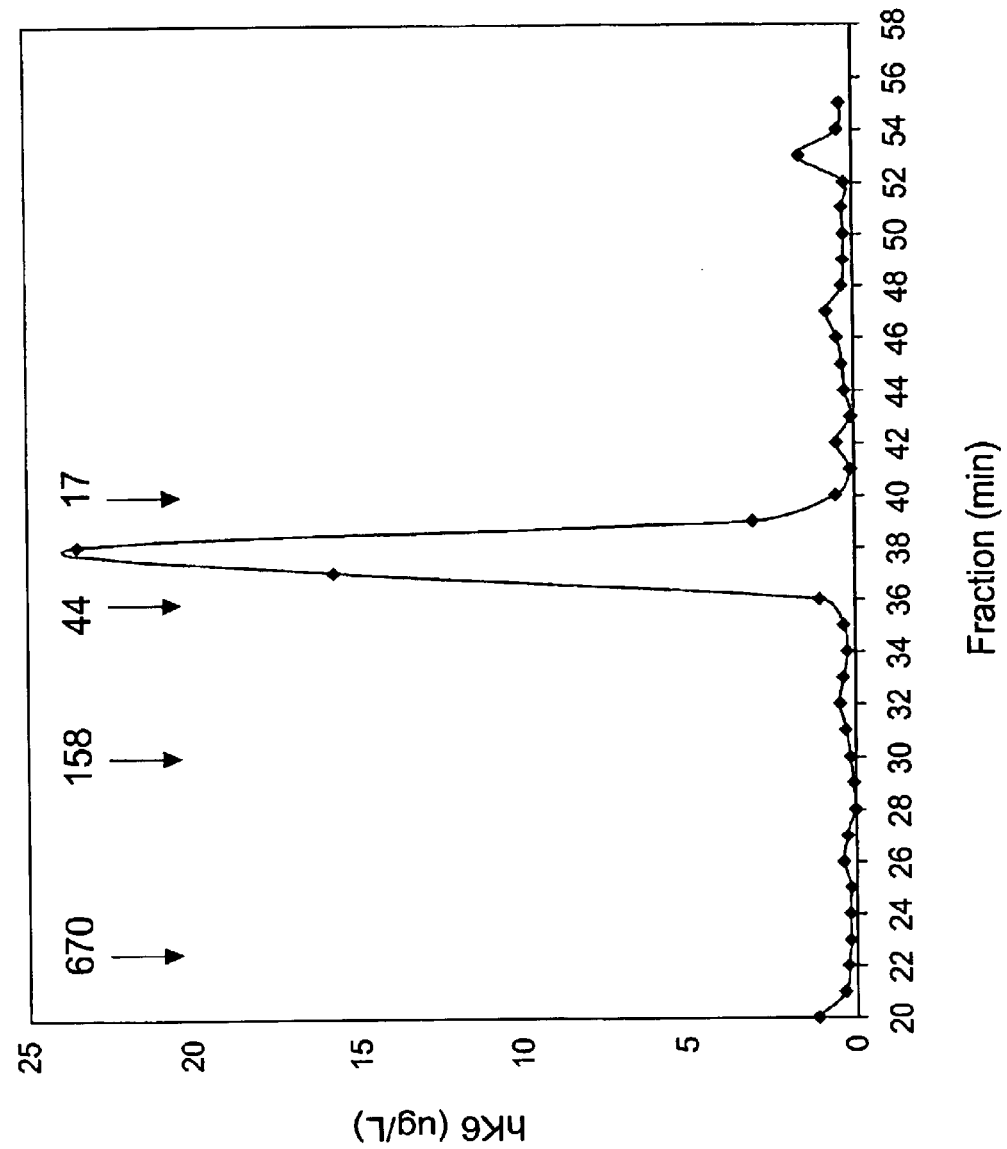
FIG. 4: High-performance liquid chromatography on a gel filtration column. Sample is whole blood of a patient with Alzheimer's disease with extremely high blood hK6 concentration (539 $\mu$g/L). There is a single immunoreactive peak eluding at fraction 38±1 which corresponds to a molecular weight of approximately 30 kDa. These data support the view that hK6 in whole blood is present in its free, uncomplexed form.

While the whole blood concentration of hK6 in all Alzheimer's disease patients was less than 61 µg/L and in all control subjects, less than 9 µg/L, one patient had a whole blood hK6 concentration of 539 µg/L. Because of the extremely high value of hK6 in this patient, this whole blood was fractionated on a size-exclusion gel filtration column to establish the immunoreactive species and the molecular weight of the detected analyte. In FIG. 4, it is shown that the whole blood of this patient contains a single immunoreactive species of an approximate molecular weight of 30 kDa, which is consistent with the molecular weight of free hK6. It was previously shown that the same molecular weight corresponds to the immunoreactive species of hK6 in serum, cerebrospinal fluid and seminal plasma and milk of lactating women (Example 1).

Figure 5:
FIG. 5: Immunohistochemical localization of hK6 in paraffin-embedded formalin-fixed brain tissue. The figure reveals intense cytoplasmic positivity of luminal aspects of the lining cells of the chorioid plexus (original magnification ×400).

Since hK6 concentration is quite high in cerebrospinal fluid, it was attempted to immunohistochemically localize the source of hK6 in cerebrospinal fluid. Various brain sections (formal in fixed, paraffin-embedded tissue) were stained with a polyclonal anti-hK6 rabbit antibody and then detected using classical immunohistochemical techniques. The highest concentration of hK6 was found in luminal cells lining the chorioid plexus (FIG. 5). It is thus possible that the bulk of hK6 production occurs in this cell type.

Discussion

The KLK6 gene encodes for a serine protease (human kallikrein 6, hK6) which is highly expressed in the central nervous system, as well as in many other organs (33). Recently, this secreted serine protease was identified in tissue extracts and various biological fluids, including serum, nipple aspirate fluid, breast cyst fluid, seminal plasma, amniotic fluid and breast cancer cytosols (Example 1). The biological role of this serine protease in the central nervous system and other peripheral organs is currently unknown. It has previously been reported that hK6 has amyloidogenic potential and may contribute to the pathogenesis of Alzheimer's disease (30). However, no data currently exist, comparing levels of hK6 in tissues or cerebrospinal fluid between Alzheimer's disease patients and normal controls. The availability of a highly sensitive method for measuring hK6 in biological fluids enabled performance of this study (34). The data, summarized in Table 2, demonstrates that the concentration of hK6 in tissue extracts is reduced in Alzheimer's disease patients, in comparison to control subjects. Additionally, there is dramatic increase of hK6 concentration in the cerebrospinal fluid and blood of Alzheimer's disease patients, in comparison to control subjects. hK6 has potential as a new biomarker for diagnosis and monitoring of Alzheimer's disease. The bulk of serum concentration of hK6 may originate from diffusion of hK6 from the cerebrospinal fluid. The increased concentration of hK6 in cerebrospinal fluid of Alzheimer's disease patients may be responsible for the increased serum concentration of hK6 in these patients. In this small group of patients, no statistically significant correlation was found between CSF and whole blood hK6 concentrations, and one patient with Alzheimer's disease had extremely high whole blood hK6 levels (FIG. 1). It is thus possible that the diffusion of hK6 from CSF to the blood may not solely depend on the concentration gradient between these two fluids but also on other factors, including permeability of the blood brain barrier.

This is the first indication that hK6 may be a new valuable biomarker for diagnosis and monitoring of Alzheimer's disease. These data may have implications for the early diagnosis and monitoring of Alzheimer's disease and may contribute to slowing the progression of this disease by allowing early diagnosis and administration of effective treatments.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

Below full citations are set out for the references referred to in the specification.

TABLE 1

Analysis of hK6 protein in various fluids

| Sample | hK6, µg/L | | | | Positivity rate |
| --- | --- | --- | --- | --- | --- |
| | Range | Mean (SD) | Median | $N^2$ | (%) |
| Milk[1] | 398–7,638 | 2,588 (1,607) | 2,531 | 20 | 100 |
| Cerebrospinal fluid (CSF) | 41–2,053 | 605 (485) | 525 | 21 | 100 |
| NAF (normal)[3] | — | 914 | — | 1 (pool) | 100 |
| NAF (cancer)[4] | — | 737 | — | 1 (pool) | 100 |
| Breast cyst fluid | 34–97 | 74 (25) | 84 | 5 (pools) | 100 |
| Male serum | 2.0–12.6 | 6.9 (2.6) | 6.7 | 18 | 100 |
| Female serum | 0–8.1 | 4.1 (2.0) | 4.4 | 18 | 100 |
| Seminal plasma | 0–17.7 | 6.8 (5.5) | 5.0 | 16 | 81 |

TABLE 1-continued

Analysis of hK6 protein in various fluids

| Sample | hK6, μg/L Range | Mean (SD) | Median | N[2] | Positivity rate (%) |
|---|---|---|---|---|---|
| Amniotic fluid | 0–9.5 | 1.1 (2.2) | 0 | 21 | 33 |
| Breast tumor cytosols | 0–33 | 2.1 (7.0) | 0 | 36 | 17 |
| Urine | 0 | 0 | 0 | 10 | 0 |

[1]From lactating women
[2]Number of samples tested
[3]Nipple aspirate fluid
[4]NAF obtained from patients with breast cancer

TABLE 2

Comparison of hK6 concentration between Alzheimer's disease and control subjects

| | Range | Mean | SD | Median | P(t-test) | P(Mann-Whitney) |
|---|---|---|---|---|---|---|
| Tissue Extracts (N = 10) | | hK6 (ng/mg) | | | | |
| Alzheimer's disease | 26–153 | 50 | 37 | 38 | | |
| Controls | 4–261 | 100 | 74 | 94 | 0.07 | 0.05 |
| Cerebrospinal Fluids (N = 10) | | hK6, μg/L | | | | |
| Alzheimer's disease | 1110–3124 | 2121 | 762 | 1969 | | |
| Controls | 141–1662 | 751 | 512 | 749 | <0.001 | 0.001 |
| Whole Blood (N = 10) | | hK6, μg/L | | | | |
| Alzheimer's disease | 0–539 | 81 | 162 | 30 | | |
| Controls | 0–9.1 | 3.6 | 3.0 | 3.0 | ND[1] | 0.002 |

ND: Not done; non-Ganssian distribution of data.

Full Citations for References Referred to in the Specification

1. Selkos D J. Translating cell biology into therapeutic advances in Alzheimer's disease. Nature 1999;399:A23–A30.
2. Dickman D W. The pathogenesis of senile plaques. J Neuropathol Exp Neurol 1997; 56: 321–339.
3. Masters C L, Simms G, Weinman N A, Multhaup G, McDonald B L, Beyreuther K. Amyloid plaque core protein in Alzheimer's disease and Down Syndrome. Proc Natl Acad Sci 1985; 82:4245–4249.
4. Goedert M. Tau protein and the neurofibrillary pathology of Alzheimer's disease. TINS 1993;16:460–465.
5. McKhann G, Drachman D, Folstein M, Katzman R, Price D, Stadlan E M. Clinical diagnosis of Alzheimer's disease: report of the NINCDS-ADRA Work Group under the autopsies of department of health and human services task force on Alzheimer's disease. Neurology1984; 34:939–944.
6. Tierney M C, Fisher R H, Lewis A J, et al. The NINCDS-ADRDA Work Group criteria for the clinical diagnosis of probable Alzheimer's disease: a clinicopathologic study of 57 cases. Neurology 1988;38:359–364.
7. Jellinger K A. Diagnostic accuracy of Alzheimer's disease: a clinicopathological study. Acta Neuropathol 1996;91:219–220.
8. Galasko D, Hansen L A, Katzman R, Weiderholt W, Masliah E, Terry R, Hill L R, et al. clinical-neuropathological correlations in Alzheimer's disease and related dementias. Arch Neurol 1994;51:888–895.
9. Andreasen N, Vanmechelen E, Van de Voorde A, et al. Cerebrospinal fluid tau protein as a biochemical marker for Alzheimer's disease: a community based follow up study. J Neurol Neurosurg Psychiatry 1998;64:298–305.
10. Galasko D. Cerebrospinal fluid levels of Aβ42 and tau: potential markers of Alzheimer's disease. J Neural Transm 1998 (suppl);53:209–221.
11. Blennow K, Wallin A, Agren H, Spenger C, Siegfried J, Vanmechelen E. Tau protein in cerebrospinal fluid: a biochemical diagnostic marker for axonal degeneration in Alzheimer's disease? Mol Chem Neuropathology 1995;26:231–245.
12. Tato R E, Frank A, Hemanz A. Tau protein concentration in cerebrospinal fluid ofpatients with dementia of the Alzheimer's type. J Neurosurg Psychiatry 1995;59:280–283.
13. Mori H, Hosoda K, Matsubara E, et al. Tau in cerebrospinal fluids: establishment of the sandwich ELISA with antibody specific to the repeat sequence in tau. Neurosci Lett 1995;186:181–183.
14. Mecocci P, Cherubini A, Bregnocchi M, et al. Tau protein in cerebrospinal fluid: a new diagnostic and prognostic marker in Alzheimer disease? Alzheimer Dis Assoc Disord 1998;12:211–214.
15. Hulstaert F, Blennow K, Ivanoiu A, et al. Improved discrimination of AD patients using β-amyloid$_{(1-42)}$ and tau levels in CSF. Neurology 1999;52:1555–1562.
16. Molina J A, Benito-Leon J, Jimenez-Jimenez F J, et al. Tau protein concentrations in cerebrospinal fluid of non-demented Parkinson's disease patients. Neurosci Lett 1997;238:139–141.
17. Ellis R J, Scubert P, Motter R, et al. Cerebrospinal fluid tau protein is not elevated in HIV-associated neurologic disease in humans. HIV Neurobehavioral Research Center Group. Neurosci Lett 1998;254:1–4.
18. Mitani K, Furiya Y, Uchihara T, Ishii K, Yamanouchi H, Mizusawa H, Mori H. Increased CSF tau protein in corticobasal degeneration. J Neurol 1998;245:44–46.

19. Urakami K, Mori M, Wada K, et al. A comparison of tau protein in cerebrospinal fluid between corticobasal degeneration and progressive supranuclear palsy. Neurosci Lett 1999;259: 127–129.
20. Arai H, Terajima M, Miura M, et al. Tau in cerebrospinal fluid: a potential diagnostic marker in Alzheimer's disease. Ann Neurol 1995;38:649–652.
21. Andreasen N, Minthon L, Clarberg A, Davidsson P, Gottfries J, Vanmechelen E, Vanderstichele H, et al. Sensitivity, specificity and stability of CSF-tau in AD in a community-based patient sample. Neurology 1999;53:1488–1494.
22. Motter R, Vigo-Pelfrey C, Kholodenko D, et al. Reduction of β-amyloid peptide42 in the cerebrospinal fluid of patients with Alzheimer's disease. Annals of Neurology 1995;38:643–648.
23. Galasko D, Chang L, Motter R, et al. High cerebrospinal fluid tau and low amyloid beta-42 levels in the clinical diagnosis of Alzheimer disease and relation to apolipoprotein E genotype. Arch Neurol 1998;55:937–945.
24. Kanai M, Matsubara E, Isoe K, Urakami K, Nakashima K, Arai H, Sasaki H, et al. Longitudi na 1 study of cerebro spinal fluid levels of tau, a beta1–40 and A beta1–42 (43) in Alzheimer's disease: a study in Japan. Ann Neurol 1998;44:17–26.
25. Andreasen N, Minthon L, Vanmechelen E, Vanderstichele H, Davidsson P, Winblad B, Blennow K. CSF-tau and CSF-Aβ42 as predictors of development of Alzheimer's disease in patients with mild cognitive impairment. Neurosci Lett 1999;273:5–8.
26. de la Monte S M, X u Y Y, Hutchins G M, Wands J R. "Increased levels of neuronal thread protein in cerebrospinal fluid of patients with Alzheimer's disease". Ann Neurol 1992;32:733–742.
27. de la Monte S M, Ghanbari K, Frey W H, Beheshti I, Averback P, Hauser S L, Ghanbari H A, Wands J R. "Characterization of the AD7C-NTP cDNA expression in Alzheimer's disease and measurement of a 41-kD protein in cerebrospinal fluid". J Clin Invest 1997;100:3093–3104.
28. Ghanbari H, Ghanbari K, Beheshti I, Munzar M, Vasauskas A, Averback P. "Biochemical Assay for AD7C-NTP in Urine as an Alzheimer's Disease Marker:. J Clin Lab Anal 1998;12:285–288.
29. Ghanbari H, Ghanbari K, Munzar M, Averback P. "Specificity of AD7C-NTP as a Biochemical Marker for Alzheimer's Disease:. Contemp Neurol 1998;4:2–6.
30. Little S P, Dixon E P, Norris F, Buckley W, Becker G W, Johnson M, Dobbins J R, et al. Zyme, a novel and potentially amyloidogenic enzyme cDNA isolated from Alzheimer's disease brain. J Biol Chem 1997;272:25135–25142.
31. Anisowicz A, Sotiropoulou G, Stemnan G, Mok S C, Sager R. A novel protease homolog differentially expressed in breast and ovarian cancer. Mol Med 1996;2:624–636.
32. Yamashiro K, Tsuruoiko N, Kodama S, Tsujimoto M, Yamamura T, Tanaka T, Nakazato H, Yamaguchi N. Molecular cloning of a novel trypsin-like serine protease (neurosin) preferentially expressed in brain. Biochem Biophys Acta 1997;1350:11–14.
33. Yousef G M, Luo L Y, Scherer S W, Sotiropoulou G, Diamandis E P. Molecular characterization of zymeprotease M/neurosin, a hormonally-regulated kallikrein-like serine protease. Genomics 1999;62:251–259.
34. Diamandis E P, Yousef G M, Soosaipillai A R, Grass L, Porter A, Little S, Sotiropoulou G. Inmunofluorometric assay of human kallikrein 6 (zyme/protease M/neurosin) and preliminary clinical applications.Clin Biochem 2000, 33: 369–375.
35. Hassapoglidou S, Diamandis E P, Sutherland D J A. Quantification of p53 protein in tumor cell lines, breast tissue extracts and serum with time-resolved immunofluorometry. Oncogene 1993;8:1501–1509.

I claim:

1. A method for diagnosing Alzheimer's disease comprising:
   (a) obtaining blood or cerebrospinal fluid from a subject;
   (b) determining the amount of human kallikrein 6 ("hK6") in said blood or cerebrospinal fluid; and
   (c) comparing said amount of hK6 detected to an amount for healthy control subjects, where detection of a statistically significant increase of hK6 compared with an amount for the healthy control subjects is indicative of Alzheimer's disease.

2. A method for diagnosing Alzheimer's disease comprising:
   (a) obtaining blood or cerebrospinal fluid from a subject;
   (b) contacting the blood or cerebrospinal fluid with an antibody specific for hK6 which is directly or indirectly labelled with a detectable substance;
   (c) determining the hK6 by measuring the amount of the detectable substance in the blood or cerebrospinal fluid;
   (d) comparing the amount of hK6 to an amount obtained for samples from healthy control subjects where a statistically significant increase in the amount of hK6 compared with the amount for the healthy control subjects is indicative of Alzheimer's disease.

3. A method as claimed in claim 2 wherein the antibody is a monoclonal antibody, a polyclonal antibody immunologically active antibody fragments, humanized antibody, an antibody heavy chain, an antibody light chain, a genetically engineered single chain F, molecule, or a chimeric antibody.

4. A method as claimed in claim 2 wherein the detectable substance is alkaline phosphatase.

5. A method as claimed in claim 4 wherein the alkaline phosphatase is detected using a fluorogenic substrate.

6. A method as claimed in claim 5 wherein hK6 is detected determined using time-resolved fluorescence.

7. A method for the diagnosis of Alzheimer's disease comprising:
   (a) obtaining blood or cerebrospinal fluid from a subject;
   (b) incubating the blood or cerebrospinal fluid with a first antibody specific for hK6 which is directly or indirectly labeled with a detectable substance, and a second antibody specific for hK6 which is immobilized;
   (c) separating the first antibody from the second antibody to provide a first antibody phase and a second antibody phase;
   (d) determining the hK6 by measuring the amount of the detectable substance in the first or second antibody phase; and
   (e) comparing the amount of hK6 with an amount obtained for samples from healthy control subjects where a statistically significant increase in the amount of hK6 levels compared with the amount for the healthy control subjects is indicative of Alzheimer's disease.

8. A method as claimed in claim 7 wherein in step (b) the first and second antibodies are contacted simultaneously or sequentially with the blood or cerebrospinal fluid.

* * * * *